United States Patent [19]

Fenocketti et al.

[11] 4,160,008
[45] Jul. 3, 1979

[54] MULTILAYERED TEST DEVICE FOR DETERMINING THE PRESENCE OF A LIQUID SAMPLE COMPONENT, AND METHOD OF USE

[75] Inventors: Leonard P. Fenocketti, Tolland, Conn.; Myron C. Rapkin, Elkhart, Ind.

[73] Assignee: Miles Laboratories, Inc., Elkhart, Ind.

[21] Appl. No.: 872,560

[22] Filed: Jan. 26, 1978

[51] Int. Cl.² ............... G01N 31/22; G01N 33/16
[52] U.S. Cl. ................. 422/56; 23/230 B; 435/4; 435/14; 435/805
[58] Field of Search ......... 23/253 TP, 230 B; 195/103.5 R, 103.5 C, 103.5 U; 116/114 AM

[56] References Cited

U.S. PATENT DOCUMENTS

| | | | |
|---|---|---|---|
| 2,249,867 | 7/1941 | Snelling | 116/114 AM |
| 3,418,083 | 12/1968 | Rey et al. | 23/253 TP |
| 3,511,608 | 5/1970 | Anderson | 23/253 TP |
| 3,802,842 | 4/1974 | Lange et al. | 23/253 TP |
| 3,814,668 | 6/1974 | Blake et al. | 23/253 TP X |
| 3,847,553 | 11/1974 | Verbeck | 23/253 TP |
| 3,901,657 | 8/1975 | Lightfoot | 23/253 TP |
| 3,907,503 | 9/1975 | Betts | 23/253 TP X |
| 3,993,451 | 11/1976 | Verbeck | 23/253 TP |
| 4,061,468 | 12/1977 | Lange et al. | 23/253 TP |
| 4,076,502 | 2/1978 | Dugle et al. | 23/253 TP |

Primary Examiner—Joseph Scovronek
Assistant Examiner—Michael S. Marcus
Attorney, Agent, or Firm—Edward H. Gorman, Jr.

[57] ABSTRACT

A test device for determining the presence of a liquid sample constituent. The device comprises a base support member having attached to it an indicator member which produces a detectable response, such as a color change, in the presence of the sample constituent. The indicator member comprises an upper reagent layer, a lower absorbent layer and a substantially sample-impervious barrier layer between the upper and lower layers. The indicator member is attached to the base member along the lower side of the absorbent layer.

16 Claims, 2 Drawing Figures

MULTILAYERED TEST DEVICE FOR DETERMINING THE PRESENCE OF A LIQUID SAMPLE COMPONENT, AND METHOD OF USE

BACKGROUND OF THE INVENTION

1. Field of the Invention

The present invention relates to a test device, and method for its use, for detecting the presence of a constituent in a test sample. Moreover, it relates to minimizing the adverse effects of misuse of the device, thereby enhancing its accuracy and dependability.

2. Discussion of the Prior Art

The art of analytical chemistry has been greatly advanced since biochemistry began emerging as a primary scientific frontier requiring increasingly sophisticated analytical methods and tools to solve problems, the solutions to which were never before attempted. Likewise, the medical profession has lent impetus to the growth of analytical chemistry, requiring both high precision and speed in obtaining results. This remarkable progress has been still further spurred by industries such as brewing, chemical manufacturing, and others.

To satisfy the needs of these expanding technologies, a myriad of analytical procedures, compositions and apparatuses have evolved, including solution chemistry techniques, automated machinery and the so-called "dip-and-read" reagent strips. It is to the last of these that the present invention is primarily directed, although substantial benefit ultimately attaches to the other procedures as well.

Reagent strip test devices enjoy wide use in many analytical applications, especially in the chemical analysis of biological fluids, because of their relatively low cost, ease of utilizability and speed in obtaining results. In medicine, for example, numerous physiological functions can be monitored merely by dipping reagent strips into a sample of body fluid, such as urine, and observing a detectable response such as a change in color or a change in the amount of light reflected from or absorbed by the strip.

Compatible with such "dip-and-read" reagent strips have arisen many chemistries for detecting body fluid components. Many of these produce a detectable response which is quantitative or at least semi-quantitative. Thus, by measuring the response after a predetermined time, the analyst can obtain not only a positive indication of the presence of a particular constituent in a test sample, but also an estimate of how much of the constituent is present. Hence, such strips provide the physician with a facile diagnostic tool as well as the ability to gauge the extent of disease or bodily malfunction.

Illustrative of such strips currently in use are products available from the Ames Company Division of Miles Laboratories, Inc. under the trademarks CLINISTIX®, MULTISTIX®, KETOSTIX®, N-MULTISTIX®, DIASTIX®, DEXTROSTIX®, and others. Test devices such as these usually comprise one or more carrier matrices, such as absorbent paper, having incorporated with them a particular reagent or reactant system which manifests a color change in the presence of a specific test sample component. Depending on the reactant system incorporated with a particular matrix, these devices can detect the presence of glucose, ketone bodies, bilirubin, urobilinogen, occult blood, nitrite, and other substances. The specific color change and the intensity of the color observed within a specific time range after contacting the strip with the sample is indicative of the presence of a particular component and its concentration in the sample. Some of these test devices and their reactant systems are set forth in U.S. Pat. Nos. 3,123,443 (CLINISTIX®); 3,212,855 (KETOSTIX®); 3,814,668, 3,164,543 and 2,981,606 (DIASTIX®); and 3,298,789, 3,092,465, 3,164,534 and 2,981,606 (DEXTROSTIX®).

It is to those of the above-described devices having more than one reagent-bearing carrier matrix that the present invention is primarily applicable. Thus, a reagent strip can contain tests for more than one constituent in a particular liquid sample. For example, a single reagent strip could consist of a reagent-bearing carrier matrix responsive to glucose in urine, and another matrix adjacent the first responsive to ketones, such as acetoacetate. Such a product is marketed by Ames Company under the name KETO-DIASTIX®. Another reagent strip marketed by Ames Company, N-MULTISTIX®, contains 8 adjacent reagent areas and provides analytical measurements of pH, protein, glucose, ketones, bilirubin, occult blood, nitrite and urobilinogen.

Despite the obvious, time-provded advantages of such multiple reagent strips as these, misuse can result in misinformation. These multiple-analysis tools comprise complex chemical and catalytic systems, each reagent area containing a unique reactive system, responsive to its particular analysate. Thus it is possible, if the reagent strip is misused, for chemicals to be transported by the liquid sample being analyzed from one carrier matrix on the strip to another. Should this happen it is possible for reagents from one carrier matrix to interfere with those of the others so contacted, causing unreliable results. Although it is common in the reagent strip industry to provide detailed instructions as to how this problem is avoided, i.e., directions for using the reagent strips, nevertheless ignorance or disregard of these instructions could permit reagents from one test area to run off onto an adjacent test area. It is to the prevention of this "run-off" problem that the present invention is primarily directed.

The solution of the run-off problem has been long sought after, but, until the advent of the present invention, never found. This solution which applicants discovered was the culmination of an extensive research effort based on their initial conception of how to avoid run-off interference, and the results are indeed unique.

Basically, it was discovered that a certain conformation of a multi-layered carrier matrix, if properly constructed, could dramatically reduce run-off interference in multiple-test reagent strips, even if the instructions for proper use of the strip were not precisely followed.

Whereas the multilayer carrier matrix which applicants invented is truly unique in the analytical arts, it can be said with certainty that multilayer matrices per se have long existed in reagent strips. U.S. Pat. No. 3,531,254 is representative of a group of patents wherein multiple layers are used for the purpose of separating reagents used in a single test. Thus potentially incompatible reagents can be impregnated into separate layers to permit extended storage periods before use. When such a multi-layered matrix is wetted with a test sample, these layers then communicate, and the reagents previously separated become mixed to give the desired analytical test.

Another example of a multi-layered carrier matrix is the one shown in U.S. Pat. No. 3,802,842. Here, a porous pad containing no reagents abuts an upper pad containing the reagents for the desired test. Thus, when liquid sample is applied to such a carrier matrix some of the sample is absorbed by the non-impregnated pad, and some by the one bearing the reagents. As in the previous patent, the layers of this carrier matrix communicate with one another when wet. Some of the liquid (and some of the reagents) pass through the upper pad into the lower pad. There is no barrier provided between the two pads.

There exist other patents which, although less pertinent than the previous two, nevertheless are of interest when considering the present invention, and are mentioned here for the convenience and information of those interested in the present teachings. U.S. Pat. No. 3,418,083 depicts an indicator-impregnated absorbent carrier matrix treated with wax, oil or similar "hydrophobic" agents. It is said that when a sample of blood is placed on such a reagent strip, only the colorless liquid components permeate it, the proteinaceous, colored blood components remaining on the surface where they can be removed. Thus, it is taught, the liquid portion bearing the analysate permeates the reagent pad, whereas colored interferants are precluded from it.

Still another prior art reference, U.S. Pat. No. 3,672,845 assigned to the present assignee, shows spraying adhesive onto a plastic or paper support member for the purpose of gluing on reagent-laden polymer particles. Yet another, U.S. Pat. No. 3,992,158, teaches an upper, semi-permeable layer containing ascorbate oxidase affixed to a lower, reagent-laden layer.

Although none of the aforementioned patents deals in any way with the run-off problem or applicants' solution of it, they represent the present extent of the applicants' knowledge of what is deemed to be the prior art most pertinent to their invention.

SUMMARY OF THE INVENTION

Briefly stated, the present invention comprises a test device and method for detecting the presence of one or more constituents of a liquid test sample. The device comprises a base support member having an indicator member affixed to it. The indicator member comprises an upper reagent layer, a lower absorbent layer and a substantially sample-impervious barrier layer between the upper and lower layers. The method comprises contacting the sample with the test device and observing any detectable response from the upper reagent layer.

Thus, the test means of the present invention can take on many forms. It can comprise a layer of absorbent material which has laminated to it, on each of its opposite faces, a substantially liquid-impervious layer, and a reagent layer overlaying at least one of the liquid-impervious layers. When one of the liquid-impervious layers is a Trycite handle, a second reagent layer can be affixed to the underside of the Trycite layer.

BRIEF DESCRIPTION OF THE DRAWINGS

FIG. 1 depicts an enlarged schematic side view of a dip-and-read type reagent strip embodiment of the present invention which is provided with a single indicator member.

FIG. 2 shows a similar side view of a dip-and-read type reagent strip having two indicator members and illustrates the run-off problem, in which sample liquid runs from one reagent matrix to an adjacent one, but is precluded from interfering with the functioning of the adjacent pad.

DETAILED DESCRIPTION OF THE INVENTION

The presently disclosed test device can be formulated to respond to a myriad of analysates, depending on anticipated use. Indicators known in the art can be provided for test sample constituents such as glucose, pH, nitrite, occult blood, bilirubin, urobilinogen, protein, ketone and others. Thus, the present invention lends itself to the detection of many possible liquid sample constituents.

Figure 1:
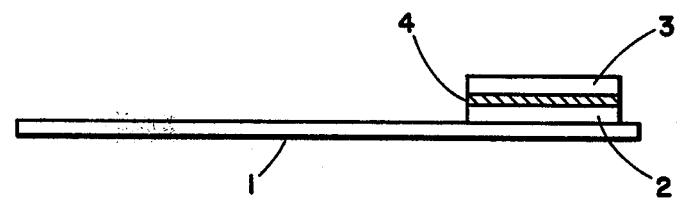
FIGS. 1 and 2 are provided to further illustrate the presently-described inventive concepts.

The test device, such as that depicted in FIG. 1, is prepared by affixing an absorbent layer 2 onto a base support member 1. Reagent layer 3 is then affixed by suitable means onto barrier layers 4 which is in turn affixed to absorbent layer 2 as shown in the drawing. This configuration has been found to be preferred, although others apparent to those skilled in the art might also prove suitable.

Figure 2:
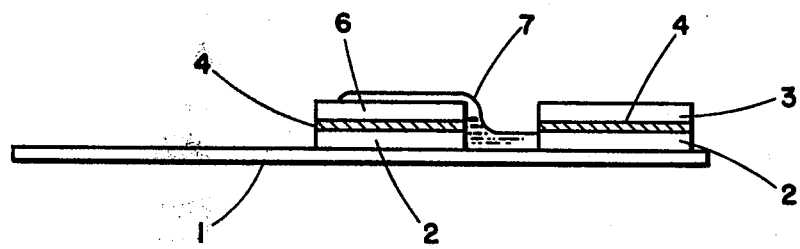

FIG. 2 serves not only to reillustrate the preferred configuration, but also to depict graphically the run-off problem and how it is solved. Thus, the base support member 1 has affixed to it two indicator members, one containing reagent layers 3 sensitive to, let us say, pH, whereas reagent layer 6 is sensitive to another sample parameter, for example protein.

Should such a multiple reagent strip be used improperly, a drop of test sample could run from one pad to another thereby contaminating the reagent layer of the adjacent pad. Thus a drop of test sample 7 could dissolve some of the reagents in upper layer 6 of one indicator member and transfer its solutes to the reagents of upper layer 3 of the other. This problem is circumvented by the structure of FIG. 2 because the drop becomes absorbed in the absorbent layers 2 under layers 3 and 6 and is thereby prevented from communicating with the upper layer 3, thus preventing the accidental indicator contamination often realized with prior art test devices.

The base support member of the present test device may take on many variations in shape, size and material of construction. Thus, it might be constructed of any substantially liquid impervious material, such as polystyrene, polyolefin, glass, paper, metal or other material. Usually, however, it is preferred that the base member be of a polymeric material such as that manufactured by E. I. DuPont de Nemours, Inc., as Trycite ®. For most purposes it has been found preferable that the support member be relatively rigid and extend sufficiently far from the reagent layer position to afford the user a convenient handle.

Absorbent layer 2 may be of any material having the capability of being wettable by the test sample. In the case where the liquid test sample is aqueous, both synthetic and natural paper-like materials have been found to be useful. Typical of these materials are Lexon ® L-5418, (a rayon, acetate, cotton blend), Novonette ® 9603 (a rayon/polyolefin blend), and Webril ® M-1165 (cotton) all of which are manufactured by the Fiber Products Division of the Kendall Co. of Boston, Massachusets; products from the C. H. Dexter Division of the Dexter Corporation known as X-2526 (nonwoven rayon fibers), 1235 (rayon/thermoplastic fiber blend), and 1148-T (blend of cellulose fibers); and, from Mead Paper Specialities of South Lee, Massachusets, paper products designated as 738, 469 and 624.

Likewise, the barrier layer 4 may be selected from numerous materials, provided that the barrier be substantially impervious to the liquid sample being tested. Examples of such materials are polyolefin film, wax, waxed paper, aluminum foil, etc. The presently preferred material for use with aqueous test samples is a double-faced adhesive tape, Type 415, from 3M Company, St. Paul, Minnesota.

The upper reagent layer may be comprised of filter paper, cloth, felt, porous ceramic, woven or matted glass fibers, polyamide fibers, and other materials known in the art for use in reagent strip analytical devices. Whichever substance is chosen (for example, absorbent paper) is incorporated with an indicator reagent system responsive to the particular test sample constituent being analyzed. Thus, if the reagent layer is to be responsive to glucose it could be incorporated with a glucose oxidase enzyme, a peroxidase enzyme and o-tolidine. Such a reagent system turns blue when contacted with a liquid sample containing glucose. The selection of the proper reagent layer material and indicator is well within the skill of the art and is easily determined in accordance with known reagent strip considerations of intended use and manufacturing requirements.

An indicator member can be affixed to base support member 1 by many suitable means. For example a double-faced adhesive tape attached on one of its sides to the bottom of absorbent layer 2 and on the other side to the base member 1 could be used. In similar fashion, curable polymeric adhesive substances currently known in the art will suffice to secure the indicator member to the base support member. Likewise any other suitable adhesive substance can be employed. Still another way is to use a porous overlayer which covers the indicator member and which is itself attached to the base member. Such an overlayer must, of course, be permeable by the test sample.

The various layers of an indicator member are affixed to each other by similar adhesive means. Thus if 3M double-faced adhesive tape Type 415 is chosen as the barrier layer 4, layers 2 and 3 are secured to it by the bottom and top adhesive faces of the type. If a polyolefinic sheet material is selected for the barrier layer, an adhesive is chosen which will bond layers 2 and 3 to the polyolefin. In any case, it is preferred to chose adhesive material having a relatively strong adhesive affinity to the barrier layer 4 and layers 2 and 3.

Although the full extent of the mechanism behind the observed effectiveness of the present invention in combating the run-off problem is not thoroughly understood, several considerations seem to play important roles. These, among others, are the thickness of the absorbent layer, and its capillary affinity to the sample liquid. Absorbent layer thicknesses ranging from about 0.1 mm to 1.25 mm were found to produce favorable results in abating run-off interference. The most favorable thickness range found was from about 0.1 to 0.5 mm.

The capillary affinity of a given absorbent layer material can be studied experimentally using the Klemm test for capillary rise. Such capillary rise measurements are useful in screening absorbent materials for use as the absorbent layer of the present invention. The experimental procedure for the Klemm test is described in the Handbook of Filtration, pages 2-13 and 2-14, First Edition (1960), published by the Eaton-Dikeman Company. The Klemm test is an empirical measurement of the time required for saturation by the sample liquid of a particular absorbent material. This property is defined as the distance that a standard sample solution will rise vertically into an absorbent material in one minute. For the present purposes the test was modified somewhat, with respect to the size of the material tested and the ingredients of the sample liquid employed.

In performing this test, a strip of absorbent material is cut to measure 5 inches in length by 1/5 inch wide. The strip is positioned vertically over a sample of liquid. The liquid comprises 0.1 grams FD&C #1 blue dye in 100 grams of water. The strip is then lowered until it contacts the liquid. The liquid is permitted to rise up the absorbent strip through capillary action for 30 seconds after contact, and the height of capillary rise is measured in centimeters.

When using the Klemm test to differentiate between various absorbent samples it is necessary that the lengthwise dimensions of the samples be measured uniformly along either the machine or cross-machine direction. Thus it will be appreciated that absorbent matrix materials generally exhibit greater capillary use in a direction parallel to the direction of material flow during its manufacture, i.e., in the machine direction, whereas capillary activity is somewhat reduced in a direction perpendicular thereto, i.e., in a cross-machine direction.

It has been found that absorbent materials having a capillary rise of about 0.1 to 5 centimeters in the cross-machine direction are useful in alleviating the run-off problem. Materials demonstrating a capillary rise of about 0.1 to 1.0 centimeters are especially useful.

As the reagent strip in FIGS. 1 or 2 is dipped into a test sample, the lower absorbent layer is exposed to the liquid only at its edges. No liquid can be absorbed by the lower absorbent layer from the reagent layer above it because of the barrier layer. Likewise the bottom surface of the absorbent layer is not available for absorption because of the presence of a liquid-impervious base support member. Thus, if the strip is dipped for a relatively short time, the upper reagent layer readily becomes saturated with test sample because of the relatively large surface thereof exposed to the sample, but the lower absorbent layer becomes only partially wetted. The absorbent layer has reserve capacity available after dipping to absorb excess liquid and guard against the aforementioned run-off problem.

EXAMPLES

The following Examples are provided to further illustrate various embodiments of the present invention. It is to be understood that they are merely exemplary of embodiments which are presently preferred, and are in no way to be interpreted as limiting the scope of the invention.

Example I—Preparation of a Protein/pH-Sensitive Strip

In constructing the reagent strip of this Example, first the lower absorbent layer was cut and attached to the base support member. Next the upper reagent layer was attached to the barrier layer, which was then attached to the top of the lower layer.

More specifically, a portion of Webril ® M-1165 cotton paper obtained from the Fiber Products Division of the Kendall Company was cut into a piece measuring 5 by 4 inches. Its thickness was 0.17 mm. To one side of this was applied a layer of double-faced adhesive tape Type 415 from 3M Company. The resulting laminate was then slit into 1/5 inch wide by 5 inch long ribbons. To a piece of Trycite plastic measuring 5 inches by 3¼ inches were applied longitudinally two of the Webril ribbons in spaced parallel relation to each other. These were attached by applying to the Trycite the remaining adhesive side of the tape attached to said ribbons.

Reagent layers were then prepared which were sensitive to pH and protein in urine. These layers comprised absorbent paper impregnated with the respective appropriate reagent systems and were identical to the reagent impregnated matrices for pH and protein found on the N-MULTISTIX® reagent strips commercially available from the Ames Company Division of Miles Laboratories, Inc. Similarly to the absorbent layers, the reagent layers were affixed by attaching sheets of reagent impregnated absorbent paper to one side of Type 415 double-faced adhesive tape, cut into 1/5 inch wide by 5 inch long ribbons, and attached in registry to the exposed (top) side of a Webril absorbent layers. One of the ribbons was prepared from pH-sensitive reagent impregnated paper and attached to the top of one of the two Webril layers via the double-faced adhesive tape, and the other ribbon was prepared from protein-sensitive reagent impregnated paper and similarly attached to the other Webril layer.

The resulting laminate comprised a Trycite base member having two indicator member ribbons attached to it, each ribbon having a lower absorbent layer of Webril, an upper reagent layer sensitive to pH or protein and a barrier layer of double-faced adhesive tape between the upper and lower layers. This laminate was then sliced perpendicular to the indicator member ribbons to form individual reagent strips, each bearing one pad responsive to pH and another responsive to protein.

This reagent strip demonstrated excellent resistance to run-off interference.

Examples II–VIII—Different Absorbent Layer Materials

Reagent strips were prepared in accordance with Example I except that different materials, both natural and synthetic were substituted for Webril as the absorbent layer. These experiments are recorded in the following Table. The reagent strips so prepared demonstrated reduction in run-off interference.

another having an absorbent layer of Mead 738 and a barrier layer of 3M Type 415 double-faced adhesive tape, and the third, having an absorbent layer of Lexon L-5418 and barrier layers of 3M double-faced adhesive. All strips had the same reagent layers as in Example I. Hence each strip had one reagent layer sensitive to pH and the other sensitive to protein.

These strips were subjected to a run-off study conducted as follows. Four reagent strips of each of the above three (i.e., no absorbent layer, Mead 738 and Lexon L-5418) were distributed to each of 10 persons chosen to conduct the study. Each person dipped the three types of strips into 30 ml aliquots of pooled urine sample and evaluated the extent of run-off interference.

The procedure established for this evaluation was simply to momentarily fully immerse the layers of each reagent strip into a urine sample and remove them immediately thereafter, making sure not to touch the sides of the urine container. The wetted strip was held vertically so that run-off from the protein reagent layer onto the pH reagent layer would be most likely to occur. The strips were held in this position for about one minute whereupon they were observed to determine the extent of run-off interference.

Run-off interference was observed as a mottling or discoloration of the pH-sensitive reagent layer caused by reagents from the protein-sensitive reagent layer. If more than 50% of the pH reagent layer was discolored by run-off, a rating of "L" (large) was assigned, "S" (small) was given if 10 to 50% of the pH reagent layer was discolored, and "N" (negligible) if discoloration was less than 10%.

Forty strips in each category were evaluated as follows:

1. Strips with no lower absorbent layer
   L–25
   S–11
   N–4
2. Strips with MEAD - 738
   L–1
   S–13
   N–26
3. Strips with LEXON - L-5418
   L–0
   S–4
   N–36

| Example | Absorbent Layer Material | Thickness (microns) | Capillary Rise (cm) Machine Dir. | x-Machine Direction |
|---|---|---|---|---|
| II | H & V 100# (Hollingsworth & Vise, Co.) | 370 | 1.2 | 0.8 |
| III | Dexter 1255 (C. H. Dexter, Co.) | 241 | 4.5 | 3.4 |
| IV | Dexter × 2526 | 150 | 1.3 | 1.3 |
| V | E & D 204 (Eaton-Dikeman Co.) | 350 | 4.2 | 3.7 |
| VI | E & D 205 | 550 | 3.8 | 3.4 |
| VII | Mead 738 (Mead Paper Co.) | 500 | 4.8 | 4.2 |
| VIII | Novonet H 819 (Kendall Co,) | 250 | 5.1 | 4.2 |

Example IX—Solution of the Run-off Problem

In order to assess the efficacy of the present invention, three reagent strips were prepared as in Example I: one having no absorbent or barrier layer (i.e. reagent layers attached directly to a Trycite support member), Clearly those reagent strips with a liquid impervious barrier layer and an absorbent lower layer were vastly less susceptible to run-off than prior art type reagent strips having no such barrier and absorbent layer.

What is claimed is:

1. Test means for determining the presence of a constituent in a liquid sample, said test means comprising a layer of absorbent material having fixedly laminated to each of the opposite faces thereof respectively, a substantially liquid impervious layer, and a reagent layer overlaying at least one of said liquid impervious layers.

2. The test means of claim 1 wherein one of said impervious layers comprises a support member comprising a projecting handle portion.

3. The test means of claim 1 wherein said reagent layer comprises an absorbent matrix incorporated with reagent means.

4. The test means of claim 2 wherein said reagent layer comprises an absorbent matrix incorporated with reagent means.

5. The test means of claim 1 wherein said absorbent layer, said reagent layer, and said impervious layer therebetween are of substantially identical size and shape in plan view and are arranged with corresponding edge portions contiguous with each other.

6. A test device for determining the presence of a constituent in a liquid sample comprising a common substantially liquid impervious support member having a flat surface, first and second layers of absorbent material fixedly laminated to said surface in spaced relation, each of said absorbent layers having a substantially liquid impervious layer fixedly laminated to the surface thereof opposite said support member, and a reagent layer overlaying each of said liquid impervious layers.

7. The test device of claim 6 wherein said reagent layers comprise different reagent systems.

8. A test device for determining the presence of a constituent in a liquid sample, the device comprising (a) a base support member having affixed thereto (b) an indicator member, the indicator member comprising an upper reagent layer, a lower absorbent layer and a substantially sample-impervious barrier layer separating said upper and lower layers, said upper and lower layers being fixedly laminated to said barrier layer.

9. The device of claim 8 in which said barrier layer is hydrophobic.

10. The device of claim 8 wherein said upper reagent layer is incorporated with an indicator substance capable of producing a detectable response in the presence of said sample constituent.

11. The test device of claim 8 wherein said barrier layer comprises a polymeric film substantially nonporous with respect to said liquid sample.

12. A test device for determining the presence of a constituent in a liquid sample, said device comprising (a) a base support member having a top side, and (b) an indicator member having a bottom side affixed to said top side of the base support member, said indicator member comprising an upper reagent layer and a lower absorbent layer, both of said layers being fixedly laminated to a substantially sample-impervious barrier layer separating said upper and lower layers.

13. A method for determining the presence of a constituent in a liquid sample comprising the steps of contacting said sample with the test means of claim 1, and observing a detectable response from said means.

14. A method for determining the presence of a constituent in a liquid sample comprising the steps of contactng said sample with the test device of claim 6, and observing a detectable response from said device.

15. A method for determining the presence of a constituent in a liquid sample comprising the steps of contacting said sample with the test device of claim 8, and observing a detectable response from said device.

16. A method for determining the presence of a constituent in a liquid sample comprising the steps of contacting said sample with the test device of claim 12, and observing a detectable response from said device.

* * * * *